United States Patent
Schnabel et al.

(10) Patent No.: US 7,807,869 B1
(45) Date of Patent: Oct. 5, 2010

(54) INCREASED RESISTANCE OF PLANTS TO PATHOGENS FROM MULTIPLE HIGHER-ORDER PHYLOGENETIC LINEAGES

(75) Inventors: Guido Schnabel, Clemson, SC (US); Ralph Scorza, Shepherdstown, WV (US); Desmond R. Layne, Seneca, SC (US)

(73) Assignee: Clemson University Research Foundation

( * ) Notice: Subject to any disclaimer, the term of this patent is extended or adjusted under 35 U.S.C. 154(b) by 0 days.

(21) Appl. No.: 11/445,450

(22) Filed: Jun. 1, 2006

Related U.S. Application Data

(60) Provisional application No. 60/686,355, filed on Jun. 1, 2005.

(51) Int. Cl.
*A01H 5/00* (2006.01)
*C12N 15/82* (2006.01)
*C12N 15/09* (2006.01)

(52) U.S. Cl. .................. 800/279; 800/278; 800/298; 435/468; 435/419

(58) Field of Classification Search ............... None
See application file for complete search history.

(56) References Cited

U.S. PATENT DOCUMENTS

| | | | |
|---|---|---|---|
| 4,459,355 A | 7/1984 | Cello et al. | |
| 4,795,855 A | 1/1989 | Fillatti et al. | |
| 4,945,050 A | 7/1990 | Sanford et al. | |
| 5,015,580 A | 5/1991 | Christou et al. | |
| 5,349,124 A | 9/1994 | Fischhoff et al. | |
| 5,459,252 A | 10/1995 | Conkling et al. | |
| 5,850,025 A | 12/1998 | Mirkov et al. | |
| 6,008,436 A | 12/1999 | Conkling et al. | |
| 6,121,512 A | 9/2000 | Siminszky et al. | |
| 6,265,638 B1 | 7/2001 | Bidney et al. | |
| 7,041,876 B2 * | 5/2006 | Beer et al. | 800/301 |
| 2002/0059658 A1 * | 5/2002 | Wei et al. | 800/278 |

OTHER PUBLICATIONS

Abstract of Article—*Isolation and Partial Characterization of an Antifungal Protein from Gastrodia elata corm*, Zhong et al., Acta Botanica Yunnanica, vol. 10, No. 4, 1988, pp. 373-380.
Abstract of Article—*Purification and characterization of a novel anti-fungal protein from Gastrodia elata*, Xu et al., Plant Physiology and Biochemistry, vol. 36, Issue 12, Dec. 1998, pp. 899-905.
Article—*Gastrodianin-like mannose-binding proteins: a novel class of plant proteins with antifungal properties*, Wang et al., The Plant Journal, vol. 25, No. 6, 2001, pp. 651-661.
Article—*Over-expression of Gastrodia anti-fungal protein enhances Verticillium wilt resistance in coloured cotton*, Wang et al., Plant Breeding, vol. 123, Issue 5, 2004, pp. 454-459.
Article—*Structural Mechanism Governing the Quaternary Organization of Monocot Mannose-binding Lectin Revealed by the Novel Monomeric Structure of an Orchid Lectin*, Liu et al., J. Biol. Chem., vol. 280, Issue 15, Apr. 25, 2005, pp. 14865-14876.

* cited by examiner

*Primary Examiner*—Medina A Ibrahim
(74) *Attorney, Agent, or Firm*—Dority & Manning, P.A.

(57) ABSTRACT

Transgenic plants, plant tissue, and propagation materials are disclosed that exhibit or convey increased resistance to pathogens of multiple higher-order phylogenetic lineages. The disclosed transgenic plants and plant tissues include plant cells containing a DNA construct encoding *Gastrodia* Anti-Fungal Protein (GAFP), also known as gastrodianin, an anti-fungal gene naturally occurring in a Chinese orchid, *Gastrodia elata*. Transgenic plants disclosed include herbaceous plants as well as woody plants, including fruit trees. Disclosed transgenic plants can also be beneficially utilized as rootstock, for instance rootstock for stone fruit crops such as peach, thereby conferring enhanced disease resistance to the rootstock without genetically altering the scion.

19 Claims, 5 Drawing Sheets

Figure 3

Root disease pathogens [a] and corresponding methodologies used for inoculation and disease assessment

| Species | Disease/pest | | | | Inoculation/Disease Assessment |
|---|---|---|---|---|---|
| | Kingdom | common name | Isolate/race | Origin | Methodology |
| Phytopthora nicotianae | Straminipila | Black shank | 011P-Tob | Clemson, SC | Roiger and Jeffers 1991 |
| Rhizoctonia solani | Fungi | Soreshin | 023R-Tob | Tifton, GA | Csinos and Stephenson 1999 |
| Ralstonia solanacearum | Eubacteria | Southern wilt | NC132 | Clemson, SC | Robertson et al. 2004 |
| Meloidegyne incognita | Metazoa | Root-knot nematode | Race 3 | Blackville, SC | Hussey and Barker 1973; Hussey and Janssen 2002 |

[a] Fungal, straminipile, and bacterial pathogens were obtained from tobacco hosts.

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggtattccac ctagccatca agcagcc                                           27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tattctctta gaccgctagt acatgga                                           27

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacaaggcgg ctacctattc                                                   20

<210> SEQ ID NO 4
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 4
ctttccgttg gttcctgatg                                                    20
```

INCREASED RESISTANCE OF PLANTS TO PATHOGENS FROM MULTIPLE HIGHER-ORDER PHYLOGENETIC LINEAGES

CROSS REFERENCE TO RELATED APPLICATIONS

This application claims benefit of Provisional Application Ser. No. 60/686,355, filed on Jun. 1, 2005.

FEDERALLY SPONSORED RESEARCH AND DEVELOPMENT

The United States Government may have rights to this invention pursuant to United States Department of Agriculture Grant No. 2002-35319-12527 (USDA/NRI seedgrant) and 2005-34103-15588 (USDA-SRIPM).

BACKGROUND OF THE INVENTION

Eukaryotic pathogens of many phylogenetic lineages can devastate crops via attack through the root structure, and the potential for damage is often not limited to a single year's crop, as many pathogens can live for years in infected soil and roots. For example, Armillaria root rot disease, caused by basidiomycete fungi from the *Armillaria* genus, is now the number one cause of peach tree death in the Southeastern United States.

Terrestrial oomycetes, the largest group of heterotrophic straminipiles, include a large number of plant pathogens and are believed to be among the most important plant pathogenic organisms that may be facultatively or obligately parasitic. These organisms include about 60 species of the genus *Phytophthora* and more than 100 species of the genus *Pythium* that are destructive plant pathogens. For instance, species of the oomycete genus *Plasmopara* are responsible for the downy mildews that affect grapes, lettuce, corn, cabbage, and many other crop plants. Species of *Phytophthora* can destroy eucalyptus, avocado, and pineapple, as well as other tropical crop plants. *P. infestans*, the *Phytophthora* species that causes late blight of potato, is well known in history. In one week in 1846, this disease wiped out almost the entire potato crop of Ireland.

Current management options for such plant pathogens are extremely limited. Since the pathogens can often survive for decades in infected root pieces or soil, crop rotation is of limited value. Furthermore, increasing environmental concern as well as expense in regard to the use of agricultural fumigants has made use of many previously common fumigants such as methyl bromide impractical.

Genetic manipulation approaches, and specifically creation of transgenic plants that exhibit increased resistance to pathogens is one approach for solving these problems. Difficulties exist with such approaches, however, as multiple transformations to protect a species from multiple pathogens is highly problematic with limited chances of successful propagation. Moreover, consumers are leery of produce that may contain the expression products of foreign DNA, and concern exists over the possible environmental impact should transgenic varieties of a plant escape into the wild, for instance through sexual reproduction mechanisms.

An anti-fungal gene has been discovered in a Chinese orchid, *Gastrodia elata* B1. F. falvida S. Chow. Specifically, the anti-fungal protein *Gastrodia* Anti-Fungal Protein (GAFP, also known as gastrodianin) was purified from the terminal corm of the orchid and shown to inhibit growth of *Trichoderma* in vitro (Hu, et al., 'Isolation and partial characterization of an antifungal protein from *Gastrodia elata* corm', Acta Bot. Yunnan 10:373-309, 1988). The protein was found to be a low molecular weight, monomeric lectin capable of binding both mannose and chitin (Xu, et al., 'Purification and characterization of a novel anti-fungal protein from *Gastrodia elata*', Plant Physio. 36:899-905). A gene expressing the protein was identified in 2001 by Wang, et al. (Gastrodianin-like mannose-binding proteins: a novel class of plant proteins with antifungal properties', Plant J. 25:651-661). (All three articles being incorporated herein by reference.) While gastrodianin has been shown to inhibit hyphal growth of several basidiomycete root rot pathogens including *A. mellea, Rhizoctonia solani*, and *Ganoderma lucidum* in vitro, the possibility of translating this anti-fungal activity to transgenic plants by incorporating the gene is not known to have been reported. Moreover, the activity of this protein when confronted with other pathogens, such as straminipile or metazoa pathogens, is not known to have been examined at all.

What is needed in the art are methods for preventing and controlling crop damage due to pathogens. In addition, what is needed in the art are crop plants that are more resistant to infection by such pathogens, and in particular, crop plants that can exhibit this increased resistance with no environmental hazard and no chance of release of a transgenic plant variety into the wild. Moreover, a single method that can simultaneously confer resistance to multiple pathogens, and in particular pathogens from multiple phylogenetic lineages, would be of great benefit.

SUMMARY

In one embodiment, the present invention is directed to methods for increasing the resistance of a plant to multiple pathogens of multiple higher-order phylogenetic lineages. For instance, the method can include cultivating a transgenic plant containing transformed plant cells, the transformed plant cells including a DNA construct encoding a gastrodianin protein in a sense orientation. In particular, the transgenic plant can be transformed from the wild-type plant so as to express a gastrodianin protein. Accordingly, the transgenic plant can exhibit increased resistance over the wild-type plant to multiple pathogens. For instance, the transgenic plant can exhibit increased resistance to fungi, straminipile, and metazoa pathogens that attack plants via the root structure of the plants and/or cause root disease in the plant. Fungi that the transgenic plants can show increased resistance to can include, for example, those of the phylum Basidiomycota or Asscomycota. The plants can also show increased resistance to root disease due to infection by oomycetes as well as nematodes.

The present invention is also directed to transgenic plants that can exhibit improved resistance to disease. For example, transgenic plants of the invention can include transgenic rootstock, fruit trees, ornamental plants, and vegetables. When considering a plant comprising a rootstock and a scion, the invention can be particularly beneficial, as the transformed cells expressing the gastrodianin protein can be confined to the rootstock, preventing the release of the transformed cells into the wild, as well as preventing the production of gastrodianin in a product that can be harvested from the scion.

Transgenic plants of the invention can also be transformed so as to express a second protein. For instance, the desired product of the plant can be the second protein, e.g., a biopharmaceutical protein, while the gastrodianin protein can confer increased resistance to the transgenic plant. In another embodiment, the second protein can confer to the plant additional resistance to disease.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures in which:

FIG. 3 is a table describing root disease pathogens from a variety of phylogenetic lineages and corresponding methodologies used for inoculation and disease assessment in Example 2;

SEQUENCE LISTINGS

Figure 1:
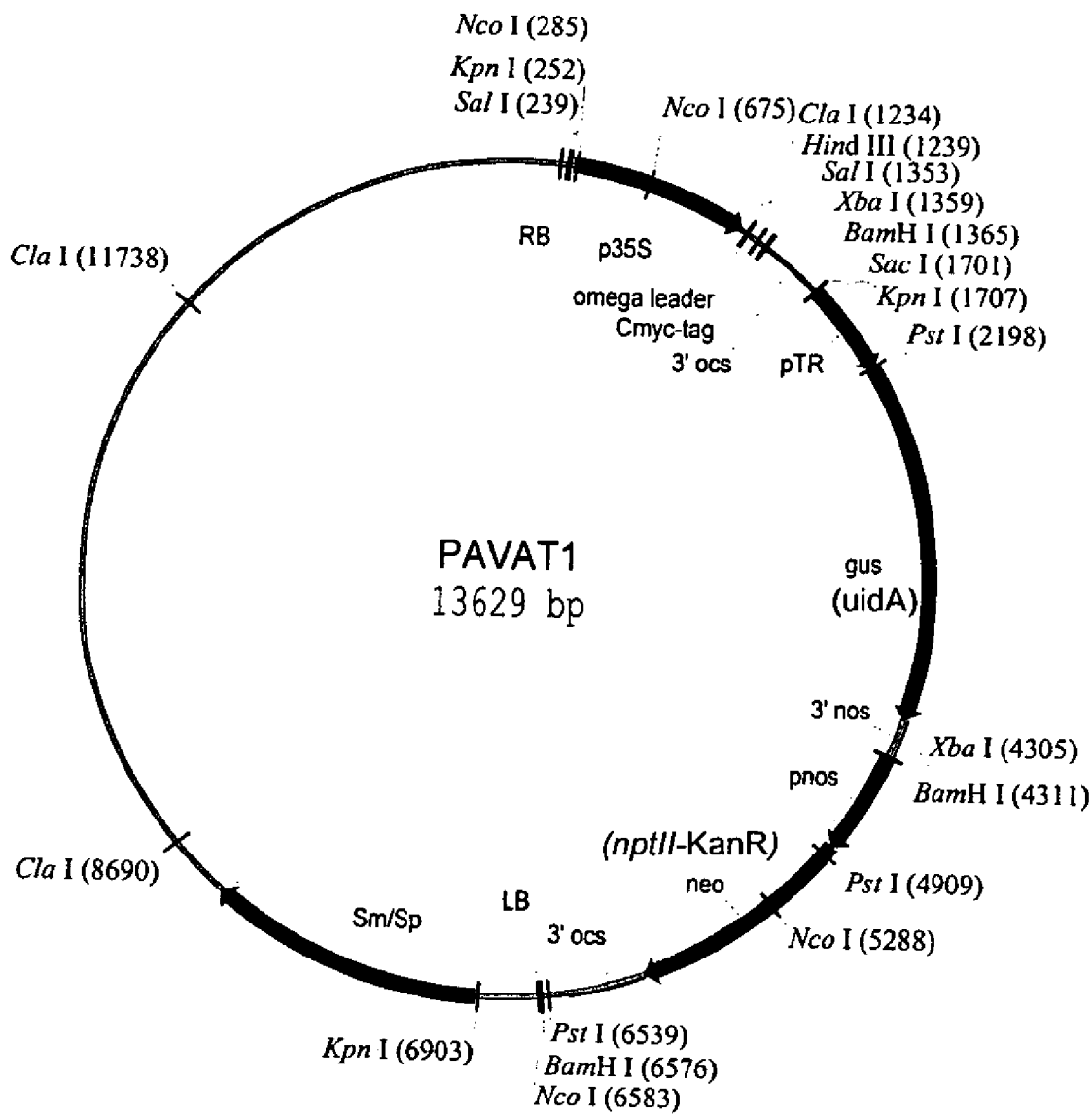
FIG. 1 provides a plasmid map of the vector pAVAT1.

SEQ ID NO: 1 depicts a GAFP-1 specific primer used in the Example section.

SEQ ID NO: 2 depicts another GAFP-1 specific primer used in the Example section.

SEQ ID NO: 3 depicts a primer used in the Example section.

SEQ ID NO: 4 depicts a primer used in the Example section.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

In one aspect, the present invention is directed to methods of increasing the resistance of plants to disease brought about due to pathogenic infection. More specifically, the methods of the present invention can confer resistance in plants to a wide variety of pathogenic organisms, and specifically, to eukaryotic organisms from different phylogenetic lineages including fungi, straminipiles, and metazoa. In other embodiments, the present invention is directed to transgenic plants formed according to the disclosed methods.

In general, the methods of the present invention include cultivating transgenic plants that express one or more gastrodianin-like proteins. The transgenic plants thus cultivated can exhibit increased resistance to multiple pathogens that attack plants via the root structure and/or cause disease in the roots. Beneficially, the transgenic plants can exhibit increased resistance to pathogens of multiple phylogenetic lineages without the utilization of expensive and possibly hazardous agricultural fumigants. In certain embodiments, the transgenic plants can be utilized as rootstock, and the scion of the plant can therefore include none of the expression product of the foreign DNA. Moreover, the use of the transgenic rootstock can confer disease resistance while preventing release of a transgenic plant into the wild through sexual reproduction.

While not wishing to be bound by any particular theory, activity of GAFP against pathogens from several distinct eukaryotic lineages is believed to be a result of the lectin's mannose-binding properties. The specific mechanism of GAFP's anti-fungal activity is still speculated, but it is known that disruption of the mannose-binding domains of GAFP by site-directed mutagenesis prevents the lectin from inhibiting fungal growth in vitro. Little is known about the specific mechanisms by which these plant lectins affect nematodes, but it is hypothesized that lectin binding interferes with either the nematode's chemosensory perception when attempting to establish feeding sites, or by binding glycoproteins in the gut causing a disruption in nematode feeding. Straminipiles like *Phytopthora* are morphologically and physiologically similar to fungi in that they obtain nutrition via an absorptive mycelium. Hence, it is theorized that mannose binding by GAFP may affect a mechanism common to the mycelial growth habit. Although the cell wall composition of *Phytopthora* is considerably different from fungi, it is known to contain mannose. Mannose residues in oomycete hyphae may play an important role in hyphal elongation or cell wall stability. In these scenarios, cell wall structure could become unstable or hyphal elongation become disrupted when hyphae come in contact with high concentrations of the lectin. Another possibility is that the mannose residues in oomycete cell walls are involved in important host-pathogen interactions. If this is the case, lectin binding could discourage infection and invasion of the host tissue giving an apparent reduction in disease symptoms in the host.

Transgenic plants of the invention can exhibit increased resistance to a wide variety of fungi, including fungi of the Phylum Basidiomycota. Exemplary basidiomycete fungi can include, for example, *A. tabescens* and *A. mellea*, which can cause *Armillaria* root rot in a variety of plants, including stone fruit trees; *S. rolfsii*, the cause of Southern Blight in legumes, crucifers, and cucurbits as well as in monocots such as alfalfa; *R. solani*, the cause of soreshin in tobacco; *G. lucidum*, the cause of *Ganoderma* rot in woody plants; *Ustilago maydis*, the causal organism of corn smut disease; and *Puccinia graminis*, the well-known stem rust or black rust on wheat and other grasses.

Other fungi to which transgenic plants of the invention can exhibit increased resistance can include Ascomycota fungi such as *Monilinia fructicola* and *Sclerotinia sclerotiorum*, as well as Ascomycota of the *Trichoderma* and *Verticillium* genera, Deuteromycota fungi such as *Fusarium. oxysporium* and Zygomycota fungi such as *Mucor*.

In addition to showing resistance to fungal infection, the transgenic plants of the invention can also resist infection by straminipiles including oomycetes such as those including, but not limited to *Plasmopara viticola*, and those of the genus *Phytophthora* including *P. cactorum, P. cinnamomi, P. citricola, P. nicotianae, P. infestans, P. sojae, P. palmivora*, and *P. tobaci*, just to name a few. Of course, these are exemplary pathogens only, and the disclosed transgenic plants are in no means limited in resistance to these examples. In particular, the disclosed transgenic plants are believed to exhibit increased resistance to infection by any pathogen that can bind gastrodianin or gastrodianin-like polypeptides, and in one embodiment, any eukaryotic pathogen that can bind gastrodianin at mannose or mannose residues existing in cells and membranes of the pathogen.

Accordingly, transgenic plants of the present invention can also exhibit increased resistance to attack by parasitizing metazoa including nematodes such as, for example, *M. incognita, D. dipsaci, M. hapla, M. javanica, R. similis, H. multicinctus, M. arenaria, P. coffeae, R. reniformis, P. anemones, A. tritici, B. avenae, S. radicicola, M. naasi, H. cajani, H. seinhorsti, T. semipenetrans, R. similis, R. citrophilus, H. arenaria, B. longicaudatus, H. trifolii, R. cocophilus, M. exigua, P. brachyurus, H. galeatus, P. vulnus, P. christiei, G. rostochiensis, G. pallida, T. primitivus, N. aberrans, A. besseyi, D. angustus, H. oryzae, P. christiei, H. glycines, H. columbus, H. schachtii, N. aberrans, H. kanayaensis, P. curvitatus, T. claytoni, G. tabacum, X. americanum*, and *C. pestis*.

According to the present invention, transgenic plants have been cultivated so as to express one or more gastrodianin proteins. For instance, transgenic plants can be cultivated via the transformation of plant cells according to any means as is generally known in the art to include a DNA construct that allows for translation and transcription of a DNA sequence, e.g., a cDNA or gDNA sequence, encoding a gastrodianin protein within the plant cell itself as well as the progeny of the plant cell.

DNA constructs that can be utilized according to the present invention can include any cDNA or gDNA that encodes a gastrodianin protein in a sense orientation. For instance, constructs suitable for use in the disclosed process can encode any gastrodianin isoform including gastrodianin-VNF protein, gastrodianin-VGM protein, gastrodianin-MGM protein, or gastrodianin-MNF protein, mRNA sequencing data of which can be found via GenBank accession numbers AJ277786, AJ277785, AJ277784, and AJ277783, respectively.

In addition to DNA encoding a gastrodianin protein in a sense orientation, DNA constructs of the invention can also include suitable operably linked regulatory sequences as are generally known to those of skill in the art. For instance, a DNA construct of the invention can include DNA encoding one or more of a suitable eukaryotic translation leader sequence, a promotor, and polyadenylation and transcription termination sequences.

For purposes of the present disclosure, the term 'leader sequence' is intended to refer to a sequence of amino acids that can direct transport of a translation product through the processing pathway of the host cell and result in the generation of the mature protein. For example, the term can refer to a sequence of hydrophobic amino acids at the amino terminus of the protein to which it is linked. DNA encoding a leader sequence is generally located downstream (3') from the start codon and upstream (5') from the DNA that encodes the gastrodianin. The leader sequence can generally include at least one amino acid that can be recognized by one or more cell proteases of the transfected cell. Such amino acids can be interposed between the leader sequence and the protein such that upon recognition of the amino acid(s) by the appropriate protease, removal of the leader sequence may be effected. The polypeptide including the leader sequence and protein together is generally referred to as a precursor protein, and the processed gastrodianin protein, absent the leader sequence, is generally referred to as the mature protein.

The DNA construct can also include a promoter to initiate translation of the DNA encoding the gastrodianin protein. Generally, any suitable promoter can be used that is capable of operative linkage to the heterologous DNA such that transcription of the DNA can be initiated from the promoter by an RNA polymerase that can specifically recognize, bind to, and transcribe the DNA in reading frame. Moreover, while promoters can include sequences to which an RNA polymerase binds, this is not a requirement. For example, promoters of the DNA constructs can include regions to which other regulatory proteins can bind in addition to regions involved in the control of the protein translation, including coding sequences. A non-limiting list of exemplary promoters encompassed by the present invention can include, but is not limited to, constitutive promoters, such as the 35S and 19S promoters of cauliflower mosaic virus (CaMV), the plant-derived ubiquitin promoter, promoters from the T-DNA genes of *Agrobacterium tumefaciens*, such as the nopaline (nos), octopine (ocs), and mannopine (mas) synthases, combinations or fusions of promoters such as the "super promoter," as well as developmentally or otherwise regulatable promoters. Other promoters suitable for use in the disclosed process include the light-inducible promoter from the small subunit of ribulose bis-phosphate carboxylase (ssRUBISCO, a very abundant plant polypeptide), and promoters of genes encoding hydroxyproline-rich glycoproteins.

In one embodiment, a promoter of the DNA construct can be a tissue-specific promoter or a promoter that can be expressed temporally or developmentally. For example, in one embodiment, root specific promoters, such as those disclosed by Conkling, et al. (U.S. Pat. No. 5,459,252, which is incorporated herein by reference) can be utilized. Other exemplary promoters include pathogen-induced promoters and/or wound-induced promoters, as are generally known in the art. These are exemplary promoters only, and it should be understood that the present invention is not limited to any particular promoter. In general, any promoter capable of controlling, either directly or indirectly, the expression of a gastrodianin-encoding DNA is encompassed by the present invention.

In one particular embodiment, the increased resistance to infection exhibited by the transgenic plants of the invention can be further enhanced through particular selection of the promoter, as is known in the art.

DNA constructs, including cDNA or gDNA encoding gastrodianin as well as one or more sequences functional for the expression, processing and secretion of the mature protein in the transgenic plant, can be designed so as to move between one or more vectors or plasmids and into the target plant cell. Accordingly, the terms 'vector' and 'plasmid' are intended to be used interchangeably and refer to elements that can be used to introduce the heterologous DNA into target cells for either expression or replication.

Suitable vectors and plasmids for use according to the present invention include those as are generally known to those of skill in the art. For instance, vectors of the present invention can include those that integrate into the host cell DNA, such as those derived from retroviruses and those derived from strains of *A. tumefaciens*, as well as those that remain autonomous, for example the RNA virus satellite tobacco mosaic virus (STMV).

There exist many known *Agrobacterium* vector systems that can be utilized in carrying out the present invention. For example, U.S. Pat. No. 4,459,355 to Cello, et al. (incorporated herein by reference) discloses a method for transforming susceptible plants, including dicots, with an *Agrobacterium* strain containing the Ti plasmid. One exemplary method for transformation of woody plants with an *Agrobacterium* vector is disclosed in U.S. Pat. No. 4,795,855 to Fillatti, et al. (incorporated herein by reference).

In one embodiment, a binary vector can be utilized for the disclosed transformation. For example, U.S. Pat. No. 6,265,638 to Bidney, et al. (incorporated herein by reference) discloses a method utilizing at least two binary *Agrobacterium* vectors in addition to a helper plasmid containing the vir region of a Ti plasmid, and can be useful in carrying out the present invention. Binary vectors such as those disclosed in Bidney, et al. can be conveniently utilized for independently introducing to a plant in an unlinked manner a second heterologous nucleotide sequence that can be either the same or different as the sequence encoding the gastrodianin. According to this embodiment, resistance to pathogenic agents can be enhanced through, for example, duplicative expression of gastrodianin and/or through expression of gastrodianin in conjunction with a second protein product.

Optionally, a second heterologous nucleotide sequence can be introduced to the plant for a purpose unrelated to the increased resistance due to gastrodianin expression. For example, a second heterologous nucleotide sequence can be introduced via a binary vector or a system such as that disclosed by Bidney, et al. via co-transformation of a plant in a single transformation event.

In one particular embodiment, co-transformation of a plant with two different heterologous nucleotide sequences can be beneficially utilized to enhance resistance to pathogens in plants that can be utilized for the desired formation of other heterological protein products. For example, the presently disclosed process can be utilized for co-transformation of tobacco plants or optionally transformation of a previously formed transgenic tobacco plant, for example, a transgenic tobacco plant that can express one or more biopharmaceuticals.

The tobacco plant has been found to be well-suited to large scale production of heterological protein products, and in particular, biopharmaceuticals, since it can be cultivated at low cost and can also generate a large volume of biomass per hectare per year. In effect, tobacco is becoming increasingly attractive as a biologically based factory to generate biopharmaceuticals in large quantity. Accordingly, in one embodiment, the presently disclosed invention is directed to transformation of tobacco that can be additionally transformed (either through a co-transformation process or separate processes, as desired) to produce biopharmaceuticals. According to this particular embodiment, transgenic tobacco plants that are cultivated for expression of a product biopharmaceutical protein can exhibit increased resistance to infection from multiple pathogens.

Multiple transformation events of a transgenic plant of the present invention is not, however, limited to tobacco. In other embodiments, the present invention is directed to transgenic plants that can be transformed with two or more heterologous sequences, one or more of which sequences can encode a gastrodianin protein for increasing resistance of the plants to infection from a plurality of pathogens.

For instance, vectors and plasmids can optionally include nucleotide sequences encoding one or more selectable markers. For example, sequences encoding selectable markers including fluorescent markers such as GFPs, GUS, S-Tags, His-Tags, and the like can be utilized.

In one embodiment, a sequence encoding a selectable marker exhibiting antibiotic or herbicide resistance can be used. For example, sequence encoding antibiotic resistant proteins such as neomycin phosphotransferase (NPTII), hygromycin phosphotransferase (HPT), or chloramphenicol acetyltransferase (CAT) can be used. Genes conferring resistance to a number of herbicide groups including, for example, the triazines, the sulfonylureas, bromoxynil, glyphosate and phosphinothricin are readily available and suitable for use as selectable markers in the presently disclosed transgenic plants. Another exemplary selectable marker is a mutant dihydrofolate reductase gene that encodes methotrexate-resistant dihydrofolate reductase. Vectors containing sequences encoding suitable resistant proteins, and the corresponding antibiotics or herbicides, are commercially available and well known to those of ordinary skill in the art. According to this particular embodiment, transformed cells can be selected out of the surrounding population of non-transformed cells by placing the mixed population of cells into a culture medium containing an appropriate concentration of the antibiotic (or other compound normally toxic to the untransformed cells) against which the selectable marker gene product can confer resistance. Thus, those cells that have been transformed can preferentially survive and multiply.

The present invention is not limited to plant cultivation via transformation systems utilizing *Agrobacterium* vector systems, and any other suitable system as is generally known in the art can optionally be utilized. For instance, as *A. tumefaciens* does not infect monocots, in other embodiments, methods as are generally known in the art can be utilized for the introduction of the sequence encoding gastrodianin into monocots.

In another embodiment, ballistic transformation methods as are generally known in the art can be utilized. For example, microparticles carrying a DNA construct of the present invention can be utilized for the ballistic transformation of a plant cell. In other embodiments, plasmid DNA can be propelled into a plant cell without particles. For instance, a DNA construct can be propelled into a plant cell to produce a transformed plant cell, and a plant can be regenerated from the transformed plant cell. Any suitable ballistic cell transformation methodology and apparatus can be used in practicing the present invention. Exemplary apparatus and procedures are disclosed in Sanford et al., U.S. Pat. No. 4,945,050, and in Christou et al., U.S. Pat. No. 5,015,580, both of which are incorporated herein by reference. Examples of microparticles suitable for use in such systems can include those utilizing spheres, for instance gold spheres, of from about 1 to about 5 µm in diameter, and the like. The DNA construct may be deposited on the microparticle by any suitable technique, for instance, by precipitation.

In yet another embodiment, methods such as those used for transformation of *Arabidopsis* involving simple absorption of plasmid DNA into the plant cell can be used.

The above described transformation methodologies are exemplary only, and in general, any method of inserting DNA into plants as is generally known in the art can be used in initially forming the transgenic plants.

The transformation processes can be directed to any suitable plant tissue. In general, the particular tissue chosen for transformation can depend upon the propagation system chosen for the species being transformed as well as on the final use of the product transgenic plant. For example, depending upon the particular plant species leaf disks, pollen, embryos, cotyledons, hypocotyls, megagametophytes, callus tissue, meristematic tissue, or meristem tissue may be preferred.

Transgenic plants encompassed by the present invention can include both monocots and dicots susceptible to infection by pathogens via the root structure. In fact, as the gastrodianin gene was initially purified from a monocot (the orchid *G. elate*) that lives parasitically off *Armillaria* mycelium it is believed that transformation of monocots according to the disclosed invention can be carried out with relatively high success rates and that gastrodianin protein will be readily produced.

In addition to tobacco, previously mentioned above, other transgenic plants encompassed by the invention include, but are not limited to, fruit, vegetable, grain, and ornamental plants such as potato, tomato, soybean, cocoa, eucalyptus, avocado, pineapple, lettuce, corn, cabbage, grape, pumpkin, squash, peanut, peas, cassava, coffee, agaves, palms, grasses, rice, wheat, barley, bamboo, sugar cane, and dates, just to name a few.

In one preferred embodiment, the present invention is directed to transgenic woody plants, including fruit, ornamental, as well as forest crops. For instance, transgenic plants of the present invention can include stone fruit trees such as peach, cherry, plum, and the like. In another preferred embodiment, the present invention is directed to herbaceous plants including transgenic fruit and vegetable crops that can exhibit increased resistance to multiple pathogens from multiple higher order phylogenetic lineages.

The present invention may be particular beneficial in forming rootstock. In addition to extending orchard life and profitability, transgenic rootstock of the present invention can be utilized to grow untransformed scion, and in one particular embodiment, to grow untransformed scion on land previously infested by a pathogen. This embodiment may be particularly beneficial, as environmental concerns as to release of the transgenic varieties into the wild as well as safety concerns in regard to existence of the transcription protein in product intended for human or animal consumption, would be mitigated, since well maintained rootstock such as may be found in orchards will not flower, and product can be produced from the untransformed scion. It should be understood that rootstock of the invention is not limited to woody plants such as fruit trees, however, and the invention can be beneficially utilized in cultivating other types of disease resistant rootstock for cultivation of vegetables such as tomatoes, melons, and the like. Moreover, rootstock of the invention can be utilized with scion of the same species or of a different, graft-compatible species, as is generally known in the art.

The transgenic plants can take any suitable form. For example, the transgenic plants can encompass chimeras including transformed cells as well as untransformed cells. In another embodiment, the transgenic plants can be clonal transformants, formed entirely of transformed cells. In addition, the transgenic plants can be propagated according to any means as is generally known in the art including clonal techniques, classical breeding techniques, or any combination thereof. For instance, transgenic plants encompassed by the present invention include those in which the added gene can be moved to new germplasm or varieties through breeding. As is known, such methods are not propagation of the original transformant but a moving of the gene or gene construct to new germplasm to develop a new variety carrying the gene or DNA construct.

Reference now will be made to exemplary embodiments of the invention set forth below. Each example is provided by way of explanation of the invention, not as a limitation of the invention.

Example 1

*E. coli* strains containing gastrodianin isoforms VNF and VGM were obtained from the Laboratorium Genetica, Gent, Belgium. The part of the cDNA that encodes each mature isoform was translationally fused to the maltose-binding protein (MBP) in the vector pMal-p2 to produce fusion proteins in *E coli* according to the methods of Wang et al. (previously incorporated herein by reference). MBP-gastrodianin fusion proteins were produced according to the manufacturer's instructions (New England Biolabs). Essentially, log-phase cultures of *E. coli* were induced for fusion protein production for 2 hours by addition of isopropyl-beta-D-thiogalactopyranoside (0.1 mM). Cells were harvested by centrifugation and the secreted MBP-fusion proteins were isolated from the periplasmic fraction by cold osmotic shock. After affinity chromatography on an amylose resin, the fusion proteins were recovered in elution buffer (20 mM Tris-HCL, pH 7.4, 200 mM NaCl, 1 mM EDTA, 10 mM maltose) and stored at −20° C. Release of gastrodianin from the fusion proteins was achieved by digestion with factor Xa (3%) in elution buffer (supplemented with 2 mM $CaCl_2$) at room temperature for 3 days. Cleavage was checked by Coomassie blue-stained polyacrylamide gels. The gastrodianin isoforms VNF and VGM were stored at −80° F. for future use.

The gastrodianin isoform VNF cDNA was inserted into the multiple cloning site of binary vector PAVAT1, a plasmid map of which is illustrated in FIG. 1. PAVAT1 is a derivative of pTHW136 (available from Plant Genetic Systems N. V., Gent, Belgium). Following insertion, the plasmid was designated pVNFbin. The VNF encoding sequence was under control of the 35S promoter and the omega leader sequence, as shown in FIG. 1.

*Agrobacterium tumefaciens* strain EHA 101 was transformed with pAVNFbin and pAVAT (empty vector control) expression plasmids, separately, using a freeze-thaw protocol for enhanced transformant recovery. Both pAVNFbin and pAVAT transformed colonies were selected on Luria Broth Agar (pH 7.0; 1 L: 10 g tryptone, 5 g Yeast extract, 10 g NaCl, 18 g agar) amended with 50 mg/L kanamycin, and 150 mg/l spectinomycin.

The presence of the GAFP-1 in selected colonies was then confirmed by PCR using GAFP-1 specific primers gafp-F (5'-GGT ATT CCA CCT AGC CAT CAA GCA GCC-3', SEQ ID NO.:1) and gafp-R (5'-TAT TCT CTT AGA CCG CTA GTA CAT GGA-3', SEQ ID NO.:2). Briefly, small amounts of individual *Agrobacterium* colonies were transferred to a PCR reaction cocktail of 50 µl total volume containing 20 µM of each primer, 200 µM dNTPs, 1.5 mM $MgCl_2$, 1.25 U of Taq DNA polymerase (Promega, Madison, Wis.), and 5.0 µl 10× reaction buffer (Promega). Cycling parameters were as follows: initial denaturation at 95° C. for 2 min (to lyse the bacterial cell wall); 28 cycles of 94° C. for 30 s, 52° C. for 30 s, and 72° C. for 40 s; final elongation at 72° C. for 10 min.

Example 2

*A. tumefaciens* strain EHA 101 containing pAVNFbin or pAVAT formed as described in Example 1 was used to transform tobacco (cv. Wisconsin 38) using a modified *Agrobacterium* cocultivation method (Burow, D. M., et al., *Plant Mol. Biol. Rep.*, 8, (1990) 124-139). Prior to transformation *A. tumefaciens* colonies were streaked out onto agarose Luria Broth agar amended with 50 mg/l kanamycin and 150 mg/l spectinomycin for selection and grown at 28° C. for 2 days in the dark. During co-cultivation, tobacco leaf tissue was sliced into approximately 3 cm square segments and punctured lightly with a scalpel to facilitate infection by *A. tumefaciens*. Generous amounts of transformed *A. tumefaciens* cells containing one of two plasmids, pAVNFbin or pAVAT, were smeared onto the leaf segments, and immediately placed onto co-cultivation media for 6 days at 28° C. After co-cultivation, inoculated plant tissue was placed on selection media with 100 mg/l kanamycin for selection and 500 mg/l carbenicillin to kill any residual *Agrobacterium* on the plant tissue. Subsequent regeneration of tobacco plants was identical to that described by Burow, et al., above.

Root and leaf tissue from GAFP-1 transgenic and control lines of *Nicotianae tabacum* (cv. Wisconsin 38) was used to characterize GAFP expression. Tissues samples were collected from two-week-old rooted tobacco cuttings and RNA was extracted according to the TRIzol method using TRIzol® Reagent (Invitrogen Corporation; Carlsbad, Calif.). RNA samples were treated with RQ1 RNase-Free DNase (Promega Corp; Madison, Wis.) to remove residual DNA and subsequently purified using the Qiagen RNeasy Mini kit for RNA purification (Qiagen; Valencia, Calif.) according to the manufacturer's instructions. Double stranded cDNA was synthesized from RNA samples using the iScript cDNA Synthesis Kit (Bio-Rad Laboratories; Hercules, Calif.) according to manufacturer's instructions.

GAFP transcription was analyzed using cDNA from tobacco lines. Quantitative real-time PCR (Q-RT-PCR) was conducted using a iCycler iQ Real-Time PCR Detection System and the Optical System Software version 3.0a (Bio-Rad Laboratories; Hercules, Calif.). Data were normalized with 18S ribosomal DNA expression using an 18S primer/competimer mix (QuantumRNA 18S Internal Standard; Ambion, Inc; Austin, Tex.). The iQ SYBR Green Supermix (Bio-Rad Laboratories; Hercules, Calif.) was used to detect GAFP gene expression according to the manufacturer's instructions. The 30-µl reactions used to amplify a portion of the GAFP gene consisted of 15 µl of the iQ SYBR Green Supermix, 5 µl of 10-fold diluted cDNA template, and 6 mM of primers gafpRT1-F (5'-CAC AAG GCG GCT ACC TAT TC-3', SEQ ID NO.:3) and gafpRT1-R (5'-CTT TCC GTT GGT TCC TGA TG-3', SEQ ID NO.:4). The 30-µl reactions using the 18S primer/competimer mix contained 15 µl of the iQ SYBR Green Supermix, 2.4 µl of primer/competimers mix (4:6 ratio), and 5 µl of 10-fold diluted cDNA template. The Q-RT-PCR cycling parameters were as follows: initial denaturation at 95° C. for 3 min; 40 cycles of 95° C. for 10 s, and 55° C. for 45 s; 95° C. 1 min, and 55° C. for 1 min. Relative quantification of gene expression was calculated using the Comparative $C_T$ method. GAFP and 18S amplicons were electrophoresed on agarose gels to verify single fragment amplifications.

GAFP translation was verified using western blot analysis. Protein fractions from the TRizol® extractions were purified according to the manufacturer's instructions (Invitrogen). SDS-PAGE was performed on purified protein samples using a Mini-Protean® 3 with 18% Tris-HCL Ready Gels (Bio-Rad Laboratories; Hercules, Calif.). Protein transfer to Immunoblot PVDF membrane (Bio-Rad Laboratories) was accomplished using a Mini Trans-Blot® electrophoretic transfer cell (Bio-Rad Laboratories). Following electrophoretic transfer, membranes were air-dried for 2 hours and rewet in methanol, followed by and water, and finally Towbin Buffer (25 mM Tris; 192M glycine; 20% Methanol; 1.0% SDS) according to the manufacture's instructions (Bio-Rad Laboratories). Immunoblotting was conducted using rabbit anti-GAFP polyclonal antisera ($1:10^4$ dilution) developed by Zymed® Laboratories (Invitrogen) and goat anti-rabbit alkaline phosphatase conjugated antibodies ($1:1\times10^7$ dilution) (Promega Corp.) according to standard methods. Detection was accomplished using Sigmafast™ BCIP/NBT tablets (Sigma Aldrich; St. Louis, Mo.). Gastrodianin signal bands from GAFP-1 transgenic tobacco and purified GAFP-1-VNF standards from several blots were converted to numerical data and analyzed using Scion Image software (Scion Corporation, Frederick, Md.) to provide a rough estimation of protein production.

Results

Six transgenic explants of *Nicotiana tabacum* containing the GAFP-1 VNF gene and one explant containing the empty vector (pAVAT) were obtained via the *A. tumefaciens* transformation. The GAFP-1-VNF expressing lines were designated VNF-1, 3, 4, 6, 7, and 10. The presence of the full length GAFP-1-VNF gene was verified by sequence analysis in each GAFP-1 transgenic line (data not shown). All transformed lines were identical in vigor to the non-transformed line (NTC) and contained the gene after clonal propagation. In a preliminary disease resistance screening, transgenic lines pAVNF-1, 3, and 10 revealed the highest resistance levels to *P. nicotianae* and therefore were used for subsequent molecular and phenotypic analyses.

Figure 2:
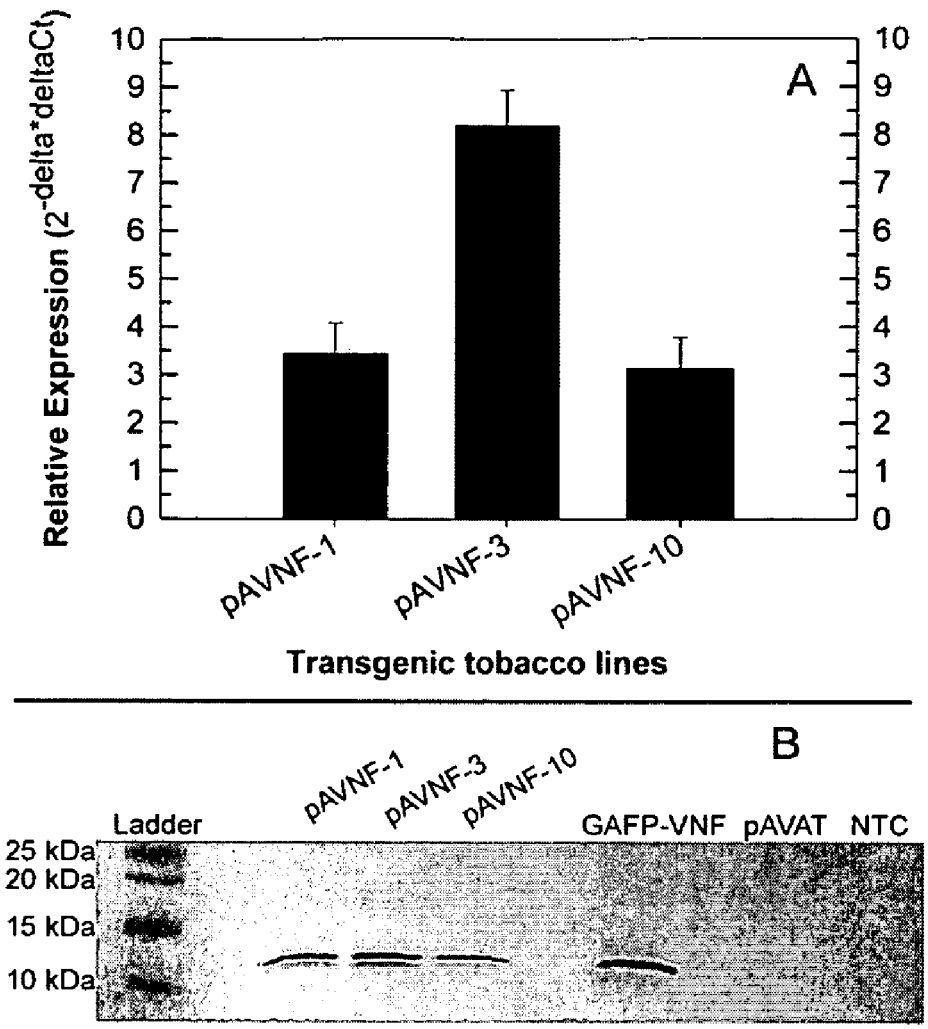
FIG. 2A graphically depicts the relative expression of gastrodianin from three transgenic tobacco lines created as described in Example 2, described herein.
FIG. 2B illustrates western blot analysis of cellular protein extracted from GAFP-1 transgenic tobacco lines of Example 2, verifying the translation of GAFP-1-VNF.

Realtime PCR indicated that the pAVNF-1, 3, and 10 lines expressed the GAFP-1 VNF gene, while the empty vector (pAVAT) and NTC line did not (FIG. 2A). Overall, pAVNF-3 was the highest expressing line, consistent across independent extractions from both root and shoot tissue, compared to lines pAVNF-1, and pAVNF-10. The presence of GAFP-1-VNF and 18S rDNA amplicons in completed Q-RT-PCR reactions was verified in GAFP-1 transgenic lines and the presence of the 18s rDNA amplicons was verified in reactions from control lines using acrylamide gel electrophoresis (data not shown).

Total cellular protein was successfully extracted and the translation of GAFP-1-VNF was verified for all GAFP-1 transgenic lines by western blot analysis (FIG. 2B). The expected 12 kDa protein band for GAFP-1 VNF was detected by immunoblotting with polyclonal anti-sera in total cellular protein extracts of lines pAVNF-1, 3, and 10, and for purified recombinant gastrodianin. Putative 12 kDa gastrodianin bands were not detected in the pAVAT or the NTC lines. Based on image analysis of signal intensity of 12 kDa bands from several additional western blots (not shown), gastrodianin production was similar among the three GAFP-1 transgenic lines and comparable to the 1 µg GAFP-VNF standard loaded on the PAGE gels.

The three most tolerant transgenic lines to *P. nicotianae*, pAVNF-1, 3, and 10, were challenged individually with four pathogens of different eukaryotic lineages as described in the table of FIG. 3. All pathogen species, isolates, or populations were isolated from or were known to infect tobacco and all inoculations were performed according to standard procedures as shown on the table of FIG. 3. Disease screening experiments were conducted on four week old rooted tobacco cuttings in a climate-controlled Biosafety Level 2 greenhouse facility. Symptom development was monitored daily for 60 days, upon which the experiments were terminated and final symptom levels were recorded. In *Phytophthora* and *Rhizoctonia* disease screening experiments, characteristic black shank and soreshin symptoms, respectively were verified and symptom severity was measured as the percentage of stem height from the crown with necrosis. Similarly, bacterial wilt symptoms caused by *Ralstonia solanacearum* were verified and symptom severity was measured as the percentage of stem height with wilted leaves or shoots. In the *Meloidegyne incognita* disease screening experiments, disease severity was measured as percent galling of the root system according to standard procedures. Disease severity measures were calculated based on observations of final symptom development from 10 plants for each tobacco line in each of three replications over time. Plants were arranged in a completely randomized design; three replications were blocks in the analysis of variance (ANOVA) (SAS version 9.1; SAS Institute Inc., Cary, N.C.). Main effects and interactions were considered statistically significant at $\alpha=0.05$.

All tobacco lines developed characteristic disease symptoms when inoculated with each of the four pathogens shown in FIG. 3. However, and as described in more detail below, transgenic lines expressing GAFP-1 VNF had reduced symptom development and improved vigor against three of the four pathogens, indicating that these plants were resistant to infection. Control plants developed more severe characteristic disease symptoms and exhibited compromised vigor compared to the GAFP-1 VNF expressing lines.

Figure 4:
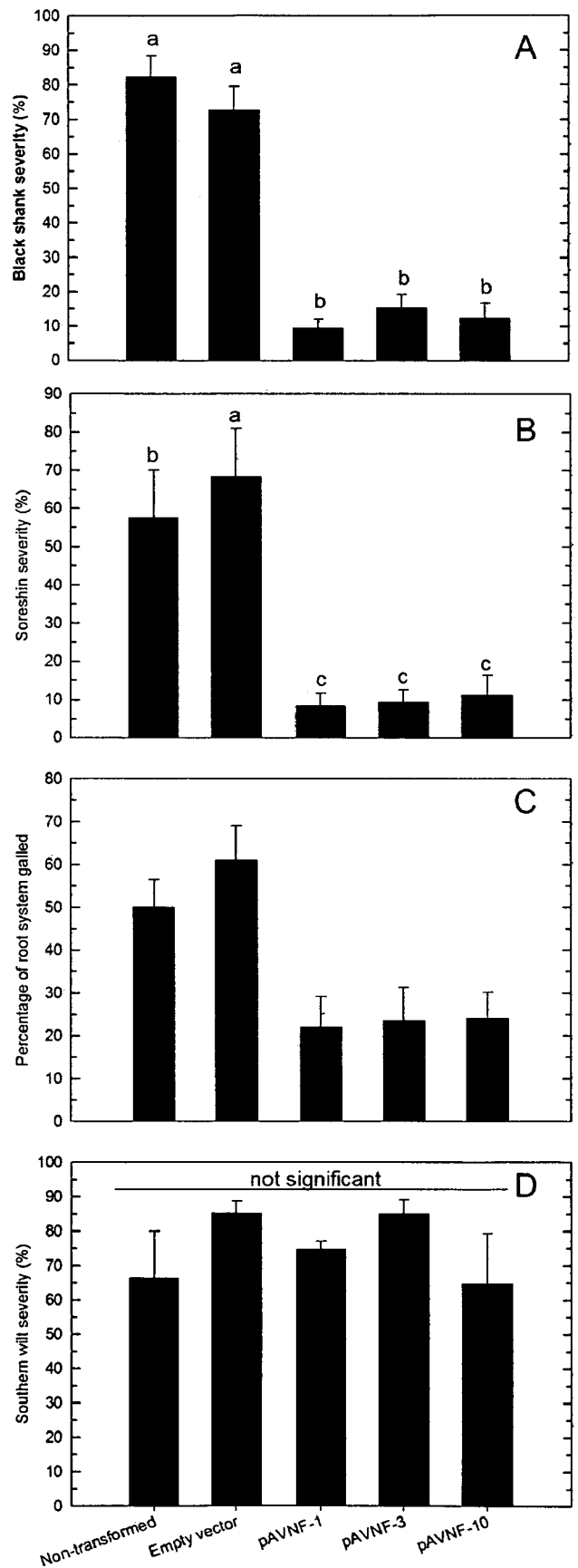
FIGS. 4A-4D graphically illustrate the response of tobacco lines described in Example 2 when confronted with the pathogens of FIG. 4.

When inoculated with *Phytophthora nicotianae*, all lines developed stem necrosis, pith discing, leaf chlorosis, and wilting symptoms, but as shown in FIG. 4A, the symptoms of GAFP-1-VNF expressing lines were significantly reduced (P<0.0001). For example, GAFP-1 transgenic lines had <15.5% stem necrosis compared with >72.7% for the two control lines. Pith discing, a characteristic black shank symptom, and ultimately death was observed for severely infected control plants but not in the three GAFP-1-VNF expressing lines. Among the GAFP-1-VNF expressing lines, there were no significant (P=0.05) differences in symptom severity. Control lines were necrotic, wilted and severally compromised in vigor, but GAFP-1-VNF expressing lines were nearly as vigorous as the uninoculated controls and were typically visually indistinguishable.

All tobacco lines inoculated with the basidiomycete *Rhizoctonia solani* developed typical Soreshin crown and stem necrosis along with browning of fine roots and reduction of root mass. Severely infected plants developed a more extensive stem necrosis shortly before or after damping off. There were highly significant (P<0.0001) differences in the severity of Soreshin necrosis between lines with GAFP-1-VNF expressing lines having <11.2% stem necrosis compared with >58.7% for the control lines, as shown in FIG. 4B. There were no significant (P=0.05) differences in symptom severity among the GAFP-1 transgenic lines. Control lines were typically necrotic, wilted and compromised in vigor, but GAFP-1-VNF expressing lines were typically visually indistinguishable from non-inoculated controls.

Plants from all tobacco lines developed root galls 60 days after root collar inoculation with the root-knot nematode *Meloidegyne incognita*. Severely galled plants were chlorotic, stunted in shoot height, and had reduced root mass. Differences in the amount of root system galling among tobacco lines were highly significant (P<0.0001) with GAFP-1-VNF expressing lines consistently having <24% of the root system galled compared with >50% for the two control lines (FIG. 4C). Among GAFP-1 transgenic lines, the amount of root system galling was not significantly (P=0.05) different. The root systems of plants from control lines typically had high levels of galling, compared to typical plants from GAFP-1 transgenic lines; however, there were some exceptions in both cases, which is reflected in the higher standard errors noted.

All tobacco lines developed wilt symptoms when challenged with the bacterium *Ralstonia solanacearum* as indicated in FIG. 4D. Severely infected plants became entirely wilted and died. Overall, there were no significant (P=0.4065) differences in the severity of wilt symptoms between GAFP-1 transgenic and control lines; wilt severity in all lines was >65%. Moreover, plants from all lines were equally wilted and compromised in vigor.

Heterologous expression of GAFP-1-VNF provided enhanced resistance to tobacco pathogens from the three eukaryotic lineages including straminipila, fungi, and metazoa. The enhanced resistance to the straminipilous pathogen, *P. nicotianae* was a surprising result, since *Urtica dioica* agglutinin (UDA), a well known anti-fungal lectin, has been shown to have no effect on the mycelial growth of *P. erythroseptica* in vitro. UDA, however, is known to have a chitin-binding mode of action, which would be ineffective against achitinous straminipiles. Constitutive expression of GAFP-1-VNF also provided increased resistance to *Rhizoctonia solani*. Although GAFP has been shown to inhibit the growth of *R. solani* in vitro, this is the first instance of a lectin transgene enhancing resistance to a basidiomycete fungus. Lastly, when challenged with the nematode *M. incognita*, GAFP expression consistently reduced root galling by 50% in GAFP-1 transgenic lines compared to control lines.

In contrast to the observed resistance to diseases caused by the eukaryotic pathogens, no enhanced disease resistance was afforded by the GAFP-1-VNF transgene against the eubacterium *Ralstonia solanacearum*. At the same time the GAFP-1 transgenic lines were no more severely impacted by *R. solanacearum* infection than the control lines. The lack of resistance against bacteria provides indirect evidence for the transgene's involvement in the resistance to infection by the eukaryotic pathogens.

Example 3

*A. tumefaciens* strain EHA 101 containing pAVNFbin or pAVAT formed as described in Example 1 was used to transform plum.

Plum seeds were collected from mature fruit. The flesh was removed from the endocarp (stone), cleaned and allowed to air dry 2-3 days at room temperature. Prior to use, the endocarp was removed with a nutcracker, seeds were surface-sterilized and soaked in sterile water overnight at room temperature. Subsequently, seed coats were removed. The radicle and the epicotyl were discarded and the hypocotyl mid-section sliced into cross sections (0.5-1 mm), which were used for regeneration/transformation.

Transformation/regeneration. Hypocotyl slices were immersed in resuspended *A. tumefaciens* for 10-20 min, blotted briefly on sterile filter paper and placed on cocultivation medium, SRM (shoot regeneration medium) without antibiotics. After two days the explants were washed in 1/2 strength MS (Mureshige and Skoog) medium with 300 mg/l timentin, blotted briefly on sterile filter paper and explanted on to SRM with 80 mg/l kanamycin and 300 mg/l timentin. When shoots first became visible (about 14 days following co-cultivation) they were transferred to SGM (shoot growth medium). When the regenerated shoots were longer than 1 cm they were separated from the supporting hypocotyl slice and cultured onto RM (rooting medium), where over 90% formed roots. Following the appearance of root initials, cultures were transferred to Magenta vessels containing sterile perlite moistened with RM. Following root elongation, plantlets were transferred to soil in a greenhouse, and exhibited a survival rate of over 90%.

Confirmation of transformation. Putative transformants identified by growth on kanamycin-containing medium were assayed using three methods to verify gene expression and incorporation. Initially, plants were evaluated for expression of the marker β-glucoronidase (GUS) using the X-glucuronide histochemical assay. Further evaluation of transformation by PCR or DNA blotting analyses required a modified CTAB DNA extraction protocol as is known in the art. PCR analyses of putative transformants was carried out using primers specific to the gene(s) of interest, in this case the gastrodianin VNF and VGM cDNA. DNA blots were probed using the non-radioactive Genius digoxigenin (DIG) labeling and detection kit (Boerhinger Manheim Corp., Ind.). The primers and probes for DNA blotting were generated by PCR using DIG dUTP in the reaction mix as described by the manufacturer.

Figure 5:
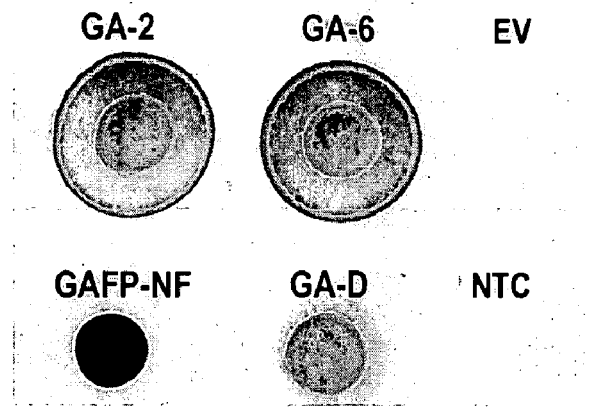
FIG. 5 is an immunoblot illustrating the presence of gastrodianin in total cellular protein extracts from plum line GA-D. Transgenic tobacco lines GA-2 and GA-6 served as positive controls, EV was the empty venctor, NTC was the non-transformed control, and GAFP-NF was the pure protein control.

GAFP protein synthesis in plum lines was verified using dot blot analysis. Referring to FIG. 5, an immunoblot illustrating the presence of gastrodianin in a total cellular protein extract from an exemplary plum line, GA-D, is shown. The absence of gastrodianin is seen in the control lines (NTC=non-transformed control and EV=empty vector). GA-2 and GA-6 were positive controls of transgenic tobacco lines. 0.5 μg purified recombinant gastrodianin (GAFP-NF isoform) was included as a standard.

Figure 6:
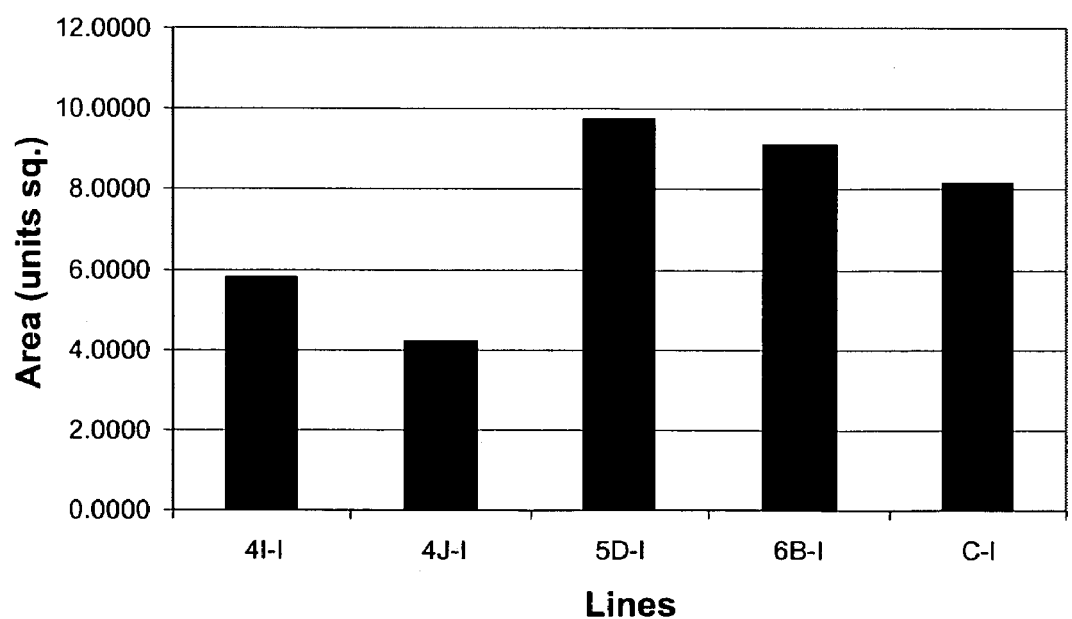
FIG. 6 graphically illustrates the response of a control line (C) and several transgenic plum lines (4I, 4J, 5D, 6B), when confronted with the pathogen *P. cinnamomi*.

Disease tolerance screening in plum. FIG. 6 graphically indicates results of disease tolerance screenings carried out on transgenic plum lines labeled 4I-1, 4J-1, 5D-1, and 6B-1 and also on a non-transformed control line, C-1. Specifically, the four plum lines were inoculated with *Phytophthora cinnamomi* and incubated for 2 weeks under conditions favoring disease. The results are graphed according to a mean area under disease progress curve, as is generally known in the art. As can be seen, two of the lines, 4I-1 and 4J-1 showed significantly increased tolerance to the disease compared to the control, C-1. In particular, lines 4*i* and 4*j* were found to develop significantly less disease compared to the control lines. Transgenic lines 5D and 6B did not indicate increased resistance, it is believed that expression of GAFP in these lines was suppressed by cell specific events.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention that is defined in the following claims and equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A method for increasing the resistance of a plant to root pathogenic oomycetes comprising cultivating a transgenic plant selected from the group consisting of fruit trees, ornamental plants, and vegetables, the transgenic plant containing transformed plant cells, the transformed plant cells including a DNA construct encoding a gastrodianin protein in a sense orientation, the gastrodianin protein selected from the group consisting of GAFP-VNF protein, GAFP-VGM protein, GAFP-MGM protein, and GAFP-MNF protein, wherein the transgenic plant has been transformed from the wild-type plant so as to express the gastrodianin protein, and wherein the transgenic plant exhibits increased resistance to pathogenic oomycetes as compared to the same type of plant that does not express the gastrodianin protein.

2. The method of claim 1, wherein the transgenic plant exhibits increased resistance to multiple pathogens that cause disease in plant roots.

3. The method of claim 1, wherein the transgenic plant further exhibits increased resistance to fungi of the phylum Basidiomycota or Ascomycota.

4. The method of claim 1, wherein the transgenic plant further exhibits increased resistance to metazoa.

5. The method of claim 1, further comprising grafting a scion to the transgenic plant, wherein the scion does not express the gastrodianin protein.

6. The method of claim 5, further comprising harvesting a crop from the scion.

7. The method of claim 6, wherein the crop is an edible crop.

8. The method of claim 1, wherein the transgenic plant has been further transformed with a heterologous second DNA encoding a second protein.

9. The method of claim 8, wherein the second protein is either a gastrodianin or a protein that is different from the gastrodianin.

10. A transgenic rootstock containing transformed plant cells, the transformed plant cells including a DNA construct encoding a gastrodianin protein selected from the group consisting of GAFP-VNF protein, GAFP-VGM protein, GAFP-MGM protein, and GAFP-MNF protein, wherein the transgenic rootstock expresses the gastrodianin protein, and wherein the transgenic rootstock exhibits increased resistance to multiple pathogens as compared to the same type of rootstock that does not express the gastrodianin protein.

11. The transgenic rootstock of claim 1, wherein the gastrodianin protein is GAFP-VNF or GAFP-VGM.

12. The transgenic rootstock of claim 11, wherein the gastrodianin protein is GAFP-VNF.

13. The transgenic rootstock of claim 10, wherein the DNA construct includes a c-DNA that encodes the gastrodianin protein.

14. The transgenic rootstock of claim 10, wherein the transgenic rootstock expresses a second protein, wherein the wild-type rootstock does not express the second protein.

15. A transgenic plant containing transformed plant cells, the transformed plant cells including a DNA construct encoding a gastrodianin protein in a sense orientation, wherein the transgenic plant expresses the gastrodianin protein selected from the group consisting of gastrodianin-VNF protein, gastrodianin-VGM protein, gastrodianin-MGM protein, and gastrodianin-MNF protein, wherein the transgenic plant exhibits increased resistance to root pathogenic oomycetes as compared to the same type of plant that does not express the gastrodianin protein, and wherein the transgenic plant is selected from the group consisting of fruit trees, ornamental plants and vegetables.

16. The transgenic plant of claim 15, wherein the gastrodianin protein is GAFP-VNF or GAFP-VGM.

17. The transgenic plant of claim 16, wherein the gastrodianin protein is GAFP-VNF.

18. The transgenic plant of claim 15, wherein the DNA construct includes a c-DNA that encodes the gastrodianin protein.

19. The method according to claim 2, wherein the transgenic plant further exhibits increased resistance to a nematode.

* * * * *